United States Patent [19]

Wahl et al.

[11] Patent Number: 4,871,678
[45] Date of Patent: Oct. 3, 1989

[54] AGENT AND PROCESS FOR THE DETERMINATION OF CALCIUM

[75] Inventors: Hans P. Wahl, Reinheim; Uwe Würzburg, Dieburg, both of Fed. Rep. of Germany

[73] Assignee: Beschrankter Haftung, Darmstadt, Fed. Rep. of Germany

[21] Appl. No.: 855,254

[22] Filed: Apr. 24, 1986

[30] Foreign Application Priority Data

Apr. 24, 1985 [DE] Fed. Rep. of Germany ....... 3514695

[51] Int. Cl.$^4$ ............................................. G01N 33/20
[52] U.S. Cl. ....................................... 436/79; 436/18; 436/19; 436/74
[58] Field of Search ....................... 436/74, 79, 18, 19; 252/408.1

[56] References Cited

U.S. PATENT DOCUMENTS

| | | | |
|---|---|---|---|
| 3,629,142 | 12/1971 | Marbach | 436/19 |
| 3,754,865 | 8/1973 | Gindler | 436/19 |
| 3,798,000 | 3/1974 | Helger | 436/74 |
| 3,822,116 | 7/1974 | Morin | 436/74 |
| 3,938,954 | 2/1976 | Stavropoulos et al. | 436/79 |
| 4,363,633 | 12/1982 | Christiansen | 436/19 |
| 4,595,677 | 6/1986 | Riniker et al. | 514/17 |

OTHER PUBLICATIONS

Elements of Quantitative Analysis, 4th Edition, Hobart et al., p. 174.

Primary Examiner—Barry S. Richman
Assistant Examiner—Wallen T. J.
Attorney, Agent, or Firm—Millen, White & Zelano

[57] ABSTRACT

An agent and process are used for the determination of calcium in liquids. The agent contains essentially ortho-cresolphthalein complexone, an acid and a zwitterionic buffer and is characterized in that the buffer contains at least one sulphonic acid amine of the general formula

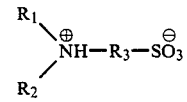

wherein
$R_1$ and $R_2$ are identical or different and denote H or alkyl, hydroxyalkyl or cycloalkyl having in each case up to 8 C atoms and
$R_3$ denotes alkyl or hydroxyalkyl having up to 8 C atoms.

18 Claims, No Drawings

AGENT AND PROCESS FOR THE DETERMINATION OF CALCIUM

BACKGROUND OF THE INVENTION

The invention relates to an agent and process for the determination of calcium in liquids, especially in body fluids.

The determination of calcium in liquids using orthocresolphthalein complexone is a customary method in many industrial and clinical laboratories. The formation of a red complex with calcium was first described in 1955 (Analyst 80, 713 (1955)). Thereafter the method has been continually modified, so that in the meanwhile it can also be carried out on systems using continuous measurement, centrifugal analyzers and instruments carrying out discrete measurements.

The reference method for the determination of calcium is atomic absorption, but this is very time consuming. Today, flame photometry is generally used for determination in serum in clinical laboratories, but this requires a suitable flame photometer because of interference by sodium ions. As a rule, photometric determinations are only suitable for determining calcium in serum; they are susceptible to trouble and do not exhibit a good agreement with atomic absorption or with determination by flame photometry. A further disadvantage of the known photometric methods of determination can be seen in the fact that potassium cyanide is used (German Patent Specification No. 2,335,350), from which on acidification, hydrogen cyanide which is lethally toxic can be formed.

A reagent for the spectrophotometric determination of calcium in the presence of a zwitterionic buffer is disclosed in U.S. Pat. No. 3,822,116. The buffer substances mentioned therein, and also glycine which is preferentially used, do not have the buffer capacity required in the pH range necessary for the color reaction, so that the sensitivity of this method is considerably reduced.

SUMMARY OF THE INVENTION

It is an object of the invention to provide an agent and process for the photometric determination of calcium ions, e.g., which both is simple to carry out, is sensitive and specific and in which both serum, plasma and urine and also, for example, effluents, can be directly employed as the sample, without pretreatment.

It is another object that this agent and/or process be capable of use in the photometers and automatic analyzers used in a routine laboratory and be in a form practicable for this purpose as far as technical use is concerned.

It is a further object of the present invention to provide a photometric process and/or agent which does not employ cyanide or toxic buffer substances, such as diethylamine and diethanolamine, since modern analyzers carry out a large number of different tests at the same time and it is therefore possible for the substances after the determination or the rinsing liquid to come into contact with acids from other tests, so that it is possible for hydrogen cyanide to be formed.

Upon further study of the specification and appended claims, further objects and advantages of this invention will become apparent to those skilled in the art.

These objects have been achieved in accordance with this invention by using a sulphonic acid amine as the zwitterionic buffer. It has been found, surprisingly, that the disadvantages described above do not occur when this buffer is used as the base.

The invention relates to an agent for the determination of calcium in liquids, containing essentially orthocresolphthalein complexone, an acid and a zitterionic buffer, which is characterized in that the buffer contains at least one sulphonic acid amine of the general formula

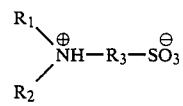

wherein
$R_1$ and $R_2$ are identical or different and denote H or alkyl, hydroxyalkyl or cycloalkyl having in each case up to 8 C atoms and $R_3$ denotes alkyl or hydroxyalkyl having up to 8 C atoms.

The invention also relates to a process for the determination of calcium in liquids by mixing the sample to be examined with orthocresolphthalein complexone, an acid and a azitterionic buffer of the general formula above and measuring the intensity of the color formed within the pH range from 9 to 11.

Preferred buffers are those of the general formula wherein $R_1$ denotes cyclohexyl or hydroxyethyl, $R_2$ denotes hydrogen and $R_3$ denotes alkyl or hydroxyalkyl having 2 to 6 C atoms, in particular (3-(cyclohexyl)-amino)-propanesulphonic acid, (2-(cyclohexyl)-amino)-ethanesulphonic acid, (3-(dihydroxyethyl)-amino)-2-hydroxypropanesulphonic acid and (3-( cyclohexyl )-amino)-2-hydroxypropanesulphonic acid and also mixtures of these componds.

In the foregoing, suitable alkyl portions in all groups mentioned for $R_1$, $R_2$ and $R_3$ include straight chained and branched moieties, e.g., methyl, ethyl, a propyl, a butyl, a pentyl, a hexyl, a hepty or an octyl group, acyclic or cyclic throughout.

The agent according to the invention contains orthocresolphthalein complexone, an acid, a buffer, if appropriate 8-hydroxyquinoline for masking magnesium ions which may possibly be present, and detergents and stabilizers. Unless indicated otherwise herein all details of the basic agent per se and its use are conventional as described, e.g., in U.S. Pat. No. 3,822,116 above.

In a preferred embodiment, the agent according to the invention comprises an acid color reagent containing orthocresolphthalein complexone, 8-hydroxyquinoline and an acid, and separately an alkaline zwitterionic buffer. The two solutions are mixed with one another before the determination in such a way that the pH value within the range from about 9 to 11 which is necessary for the color reaction is reached.

The acid color reagent generally contains 0.01 to 1 g/l of orthocresolphthalein complexone, 0 to 5 g/l of 8-hydroxyquinoline and 0.01 to 0.3 mol/l of an acid which is compatible with the other constituents of the test and which does not interfere with the color reaction. The acid is added in such an amount that a pH within the range from 0.5 to about 3 is achieved in the final solution. The acids which can be employed are either mineral acids, such as hydrochloric acid, sulphuric acid, nitric acid or phosphoric acid, or solid, non-volatile acids, such as potassium bisulphate, sulphosalicylic acid, naphthalenesulphonic acid, naphthalenedisulphonic acid, salicylic acid, acetylsalicylic acid, citric acid or tartaric acid. Solid acids are particularly necessary if the color reagent is employed in a lyophilized form, as a tablet or bound to a carrier. The color reagent, which has been prepared in dry form, is rendered ready for use by the addition of a solvent to achieve the foregoing concentrations. The solvent can be for example, water, the sample itself or another aqueous compatible solvent such as a buffer solution and mixtures of these solvents with alcohols.

The azitterionic buffer solution is prepared separately. It contains the buffer substance in a concentration 0.05 to 1 mol/l and, if appropriate, a wetting agent, such as a polyoxyethyl ether or polyethylene glycol monoalkyl ether. Wetting agents are recommended in case of turbid samples.

The pH of the buffer solution is adjusted to the required alkaline value by means of an alkali solution, for example sodium hydroxide solution. The required alkaline pH and the amount of alkali are those necessary to produce mentioned pH range of 9-11 necessary for the color reaction when the buffer solution is mixed with the other portion of the reagent. Typical values are 9.8.–10.9.

This reagent can be employed in the form of a solution; it can also be in the form of a lyophilizate, or in a tablet form or attached to a carrier, such as paper, glass fibers, wool, plastics, plastic foams and the like, and in this case is rendered ready for use by the addition of a solvent. The solvent can be biological fluid to be determined or another solvent. When both portions are in the solid form, relative amounts are used to achieve concentration values and a pH range as described above, or such proper amounts are formulated together to form a single entity.

For the determination of calcium ions, the color reagent and the buffer are combined in a suitable form, the sample is added and the intensity of the color complex formed is determined photometrically at a wavelength of 540 nm. A preferred solution ready for use contains, for example, 0.02 to 0.5 g/l of orthocresolphthalein complexone, 0.5 to 2.5 g/l of 8-hydroxyquinoline, 0.01 to 0.2 mol/l of hydrochloric acid, 0.01 to 5 g/l of a polyoxyethylene ether and 0.05 to 1 mol/l of the buffer according to the invention, the pH of which has previously been brought to a value within the range from about 10 to 11.8 by means of sodium hydroxide solution.

Typically, 150-2500 μl of the final reagent are employed in conjunction with a 1-50 μl sample containing amounts of Ca which are usually in the range of 0-20 mmole/l. these amounts are not critical as long as the foregoing considerations are met. The test can be carried out at 15°-40° C., preferably at about room temperature.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

EXAMPLES

Example 1

The following calcium reagent mixture was prepared:

| Color reagent: | |
|---|---|
| Ortho-cresolphthalein complexone | 0.1 mmol/l |
| 8-Hydroxyquinoline | 6.0 mmol/l |
| Hydrochloric acid, pH 2 | 0.01 mol/l |
| Buffer: | |
| (3-(Cyclohexyl)-amino)-propanesulphonic acid | 0.2 mol/l |
| Polyoxyethylene ether | 2.0 g/l |
| NaOH, pH 10.7 | |

The reagents were mixed in a 1:1 ratio, a pH of 9.8 being reached thereby.

The determination was carried out by pipetting the following amounts into cells:

| | Reagent blank value | Standard | Sample |
|---|---|---|---|
| Water | 10 μl | — | — |
| Standard | — | 10 μl | — |
| Sample | — | — | 10 μl |
| Reagent mixture | 1,000 μl | 1,000 μl | 1,000 μl |

The solutions were mixed in the cell, and the extinction at a wavelength of 540 nm was read off after one minute, at 37° C. The extinction was stable for at least 30 minutes. The concentration of calcium ions was determined by deducting the blank value of the extinction of the reagents from the extinction of the standard and the samples. The concentration of calcium is therefore calculated as follows:

$$\text{Calcium concentration} = \frac{\text{Extinction of sample}}{\text{Extinction of standard}} \times \text{Concentration of the standard}$$

A comparison of the values for calcium determined by this method with the values given by flame photometric measurement shows a strictly linear correlation, as can be seen from the following table:

TABLE I

| Determination by flame photometry Ca concentration [mmol/l] | Determination by photometry Extinction: 540 nm |
|---|---|
| 1.00 | 0.1330 |
| 2.01 | 0.2650 |
| 3.00 | 0.4000 |
| 4.02 | 0.5332 |
| 4.98 | 0.6650 |
| 10.00 | 1.3286 |

EXAMPLE 2

The following calcium reagent mixture was prepared:

| Color reagent: | |
|---|---|
| Ortho-cresolphthalein complexone | 0.1 mmol/l |
| 8-Hydroxyquinoline | 6.0 mmol/l |
| Potassium bisulphate | 0.06 mol/l |
| Zwitterionic buffer: | |
| (3-(Cyclohexyl)-amino)-2-hydroxypropane-sulphonic acid | 0.2 mol/l |
| Polyethylene glycol monoethyl ether | 2.0 g/l |

-continued

NaOH, pH = 10.7

The reagents were mixed in a 1:1 ratio; the determination was carried out analogously to Example 1.

A comparison of the calcium values determined by means of this reagent with the values obtained from a reagent containing glycine instead of the buffer according to the invention shows that the sensitivity of the new agent is appreciably higher than with the known agent.

TABLE II

| Ca concentration [mmol/l] | Buffer according to the invention, E = 540 nm | Glycine as buffer, E = 540 nm |
| --- | --- | --- |
| 2 | 0.2640 | 0.0660 |
| 4 | 0.5278 | 0.1310 |
| 6 | 0.7924 | 0.1902 |
| 8 | 1.0560 | 0.2488 |
| 10 | 1.3203 | 0.3006 |

EXAMPLE 3

Discs (diameter 18 mm; height 8 mm) were bored out of polyurethane foam MA 5044 made by Metzeler, Memingen. These discs were extracted by boiling for 2 hours in 10% strength sodium carbonate solution and were then rinsed several times with distilled water and dried. A carrier test pack was prepared by impregnating two of these discs with the following color reagent solution (200 ul) and azitterionic buffer solution (200 μl), respectively.

| Color reagent: | |
| --- | --- |
| Ortho-cresolphthalein complexone | 0.5 mmol/l |
| 8-Hydroxyquinoline | 30.0 mmol/l |
| Potassium bisulphate | 0.3 mmol/l |
| Zwitterion buffer: | |
| (3-(Cyclohexyl)-amino)-2-hydroxy-propanesulphonic acid | 0.5 mol/l |
| Polyethylene glycol monoethyl ether | 10.0 g/l |
| NaOH, pH = 10.7 | |

The discs were dried in vacuo. One disc containing color reagent and one disc containing zwitterionic buffer were inserted in a disposable syringe (diameter 18 mm) to make each test set-up. 1 ml of water was then sucked several times into the disposable syringe prepared in this way and was discharged and then put into a cell together with the sample. Measurement and evaluation were carried out analogously to Example 1. The same results were obtained as in Example 1.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. An agent useful for determining calcium in a liquid, comprising an effective amount for determining the presence of calcium of orthocresolphthalein complexone, an acid and a zwitterionic buffer which is at least one sulphonic acid amine of the formula

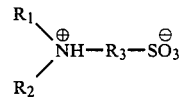

wherein $R_1$ is H, alkyl, hydroxyalkyl or cycloalkyl each having up to 8 C atoms, $R_2$ is H, alkyl, hydroxyalkyl or cycloalkyl each having up to 8 C atoms, and $R_3$ is alkyl or hydroxyalkyl each of up to 8 C atoms.

2. An agent of claim 1 in solution form wherein the concentrations are about 0.01 to 1g/l of orthocresolphthalein complexone, about 0.01 to 0.3 mol/l of the acid and about 0.05 to 1 mol/l of the sulfonic acid amine.

3. An agent of claim 2 wherein the solution of orthocresolphthalein complexone further comprises an amount up to about 5 g/l of 8-hydroxyquinoline.

4. An agent of claim 2 wherein the pH of the acid-containing solution is about 0.5 to 3.

5. An agent of claim 4 wherein the acid is a mineral acid or potassium bisulphate, sulphosalicylic acid, naphthalenesulphonic acid, naphthalenedisulphonic acid, salicylic acid, acetylsalicylic acid, citric acid or tartaric acid.

6. An agent of claim 1 comprising one solution containing all of said components, said solution having a pH of about 9 to 11.

7. An agent of claim 1, wherein the sulfonic acid amine is (3-(cyclohexyl)-amino)-propanesulphonic acid, (2-(cyclohexyl)-amino)-ethanesulphonic acid, (3-(dihydroxyethyl)-amino)-2-hydroxypropanesulphonic acid, (3-(cyclohexyl)-amino)-2-hydroxypropanesulphonic acid or a mixture thereof.

8. An agent of claim 1 in solid form.

9. An agent of claim 8 wherein the components thereof are attached to an inert carrier.

10. An agent of claim 1 comprising a solution of orthocresolphthalein complexone and 0.05 to 1 mol/l of the sulfonic acid amine, said solution having a pH of 9–11.

11. An agent of claim 1, comprising one solution containing all of said components, said solution having a pH of from 9.8 to 10.9.

12. An agent of claim 1, wherein cyanide is not present.

13. A process for the determination of calcium in a liquid sample comprising mixing the sample to be examined with an agent comprising an effective amount for determining the presence of calcium of orthocresolphthalein complexone, an acid and a zwitterionic buffer which is at least one sulphonic acid amine of the formula

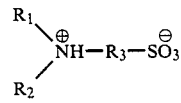

wherein $R_1$ is H, alkyl, hydroxyalkyl or cycloalkyl each having up to 8 C atoms, $R_2$ is H, alkyl, hydroxyalkyl or cycloalkyl each having up to 8 C atoms, and R3 is alkyl or hydroxyalkyl each of up to 8 C atoms to form a mixture of pH of 9 to 11 to obtain a color and determining the presence of calcium by measuring the intensity of the resultant color.

14. A process of claim 13 wherein said mixture is formed by mixing with said sample orthocresolphthalein complexone and the acid and a separate solution of the buffer.

15. A process of claim 13 wherein said mixture is formed by adding said agent in solid form to the sample.

16. A process of claim 13 wherein said measuring step is conducted photometrically at a wavelength of about 540 nm.

17. A process for the determination of calcium in a liquid sample comprising measuring the intensity of the color which results in an admixture of the sample to be examined and an agent comprising an effective amount for determining the presence of calcium of orthocresolphthalein complexone, an acid and a zwitterionic buffer which is at least one sulphonic acid amine of the formula

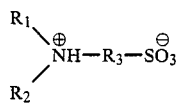

wherein
  $R_1$ is H, alkyl, hydroxyalkyl or cycloalkyl each having up to 8 C atoms,
  $R_2$ is H, alkyl, hydroxyalkyl or cycloalkyl each having up to 8 C atoms, and
  $R_3$ is alkyl or hydroxyalkyl each of up to 8 C atoms, said admixture having a pH of 9–11, and determining the presence of calcium by measuring the intensity of the color.

18. A process for the determination of calcium in a liquid sample comprising mixing the sample to be examined with an agent comprising an effective amount for determining the presence of calcium of orthocresolphthalein complexone, an acid and a zwitterionic buffer which is at least one sulphonic acid amine of the formula

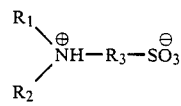

wherein
  $R_1$ is H, alkyl, hydroxyalkyl or cycloalkyl each having up to 8 C atoms,
  $R_2$ is H, alkyl, hydroxyalkyl or cycloalkyl each having up to 8 C atoms, and
  $R_3$ is alkyl or hydroxyalkyl each of up to 8 C atoms, wherein the sulphonic acid amine is present in an amount of 0.05 to 1 mol/l, wherein said mixture which is formed has a pH of 9 to 11 and a color, and determining the presence of calcium by measuring the intensity of the color.

* * * * *